United States Patent [19]

Le Du et al.

[11] 4,383,879

[45] May 17, 1983

[54] CEMENT FOR THE FIXATION OF OSSEOUS PROSTHESES

[75] Inventors: Antoine Le Du, Livry-Gargan; Frantz Langlais, Paris; Christian Michaud, Chelles; Michel Postel, Paris, all of France

[73] Assignee: Commissariat a l'Energie Atomique, Paris, France

[21] Appl. No.: 245,709

[22] Filed: Mar. 20, 1981

[30] Foreign Application Priority Data

Mar. 24, 1980 [FR] France ............................ 80 06479

[51] Int. Cl.$^3$ .......................................... C08L 63/02
[52] U.S. Cl. ............................... 156/307.7; 156/330; 156/334; 523/118; 523/400; 523/451; 523/457
[58] Field of Search .................. 260/37 EP; 525/118, 525/122, 532, 911; 424/78; 523/118, 428, 457, 451, 400; 524/414; 156/307.7, 330, 334

[56] References Cited

U.S. PATENT DOCUMENTS

| | | | |
|---|---|---|---|
| 2,951,778 | 9/1960 | Haberlin | 260/37 EP |
| 3,532,653 | 10/1970 | Smeal | 260/37 EP |
| 3,707,583 | 12/1972 | McKown | 260/37 EP |
| 3,926,903 | 12/1975 | Scola | 260/37 EP |
| 4,012,458 | 3/1977 | Wada et al. | 260/37 EP |
| 4,129,670 | 12/1978 | Riew | 260/37 EP |

Primary Examiner—Lewis T. Jacobs
Attorney, Agent, or Firm—Michael N. Meller; Anthony H. Handal

[57] ABSTRACT

The present invention relates to a cement which may be used for the fixation of osseous prostheses. This cement is obtained by hardening of a mixture comprising:
(a) at least one epoxide resin having a high reactivity and a very low toxicity, consisting of a diepoxide of a glycidyl ether of bisphenol A;
(b) a reactive, non-toxic suppling resin, consisting preferably of hydroxyl-terminated polybutadiene;
(c) a mineral filler in powder form;
(d) a hardener capable of reacting with said epoxide resin to effect hardening thereof, and
(e) a hardening accelerator.

The invention is more particularly applicable to the fixation of hip prostheses.

13 Claims, No Drawings

CEMENT FOR THE FIXATION OF OSSEOUS PROSTHESES

BACKGROUND OF THE INVENTION

The present invention relates to a cement for the fixation of osseous prostheses.

It is known that the problems raised by the treatment of diseases such as arthrosis or degenerative joint disease of the hip have in recent years been able to be solved by surgical operations which consist in removing the affected parts of the joint and in replacing them by metal, ceramic or plastic prostheses in order to provide the coefficients of friction compatible with correct functioning of the joint. In the case of the hip, the prostheses are fixed, on the one hand, in the medullary cavity of the femur and, on the other hand, in the acetabulum of the pelvis.

Up to the present time, this fixation has been effected by means of polymer cements, obtained by mixing a methyl polymethacrylate powder with monomer methyl methacrylate, a catalyst and possibly barium sulfate as opaquing agent.

However, such cements are not completely satisfactory from the medical point of view; in fact, methyl methacrylate has a certain toxicity; furthermore, too much heat is emitted when these cements harden, this leading to relatively high temperatures of the order of 80° to 90° C. and, in addition, there is a phenomenon of shrinkage during polymerization.

On this subject, it should be noted that the use of cements based on synthetic resins raises certain problems due to the exothermicity of the hardening reactions and the phenomena of shrinkage of the resin during hardening. Thus, although cements based on synthetic resins have already been used in other fields, particularly in the dental field, said cements are generally not suitable for the fixation of osseous prostheses, as the characteristics required for these two uses are different. In fact, for the fixation of osseous prostheses, shrinkage of the resin must be reduced as far as possible and it is necessary to use cements of which the hardening does not lead to a reaction which is too exothermic in order to limit the heating all the more so as, in this case, larger quantities of cement are used than in the dental domain. Furthermore, for the fixation of osseous prostheses, it is necessary to use cements capable of hardening in a moist medium whilst in the dental art the problem is not the same, since it is possible to use local drainage techniques.

Finally, for the fixation of osseous prostheses, the consistency of the cement is of great importance to obtain a rapid and sure positioning of the cement between the elements to be fixed. Moreover, it is advantageous to obtain the hardening of the cement relatively rapidly once it is placed in position.

SUMMARY OF THE INVENTION

It is precisely an object of the present invention to provide a cement for the fixation of osseous prostheses which enables the above-mentioned problems to be solved.

This cement is characterized in that it is obtained by hardening of a mixture comprising:
(a) at least one epoxide resin having a high reactivity and a very low toxicity, consisting of a diepoxide of a glycidyl ether of bisphenol A;
(b) a reactive and non-toxic suppling resin consisting of a polymer comprising a plurality of reactive functions chosen from the group comprising the amine, carboxy, hydroxy and epoxy functions;
(c) a mineral filler in powder form;
(d) a hardener capable of reacting with said epoxide resin to effect hardening thereof, and
(e) a hardening accelerator;

the mixture comprising for 100 parts by weight of the mixture of epoxide resin and suppling resin, 50 to 85 parts by weight of mineral filler, 10 to 20 parts by weight of hardener and 5 to 10 parts by weight of hardening accelerator.

The epoxide resin and the suppling resin advantageously have a low viscosity, for example of the order of 200 poises.

The mixture of epoxide resin and of suppling resin preferably comprises at the most 8% by weight of suppling resin.

Due to the presence of these different constituents, in the proportions indicated hereinabove, the cement of the invention has the desired properties to obtain the fixation of osseous prostheses under good conditions.

Firstly, it has a consistency perfectly adapted to this use, i.e. the consistency of mastic, this facilitating its positioning and rendering it compatible with the modus operandi.

Furthermore, the use of a mixture of epoxide resin and of reactive suppling resin enables the mechanical properties of the hardened cement to be modified and adapted, in particular increases its suppleness and, moreover, avoids the phenomena of shrinkage, this rendering it particularly adapted to the fixation of osseous prostheses as, in this case, shrinkage is incompatible. Moreover, due to the choice of the different constituents of the mixture, a low emission of heat during hardening of the cement is obtained, as the reaction is not very exothermic.

Thus, the temperature may be limited to 55° C. during hardening, which constitutes a considerable advantage for the fixation of osseous prostheses being given the relatively large quantities of resin employed.

Moreover, the cement according to the invention presents the advantage of not being toxic, of being compatible in the long run with the biological medium, of being rapidly hardenable (about 10 mins.) and of having good mechanical properties which remain stable in the course of time.

Finally, the constituents of this cement may easily be sterilized without degradation, and may be packed separately, for a long time, being predosed so as to facilitate the surgeon's task and avoid any error or dosage at the moment of use.

According to the invention, the choice of an epoxide resin having a high reactivity and low viscosity, preferably of the order of 200 poises, mixed with a suppling resin, makes it possible to obtain a very reactive mixture which may be hardened in the presence of water. Furthermore, the addition of a suitable hardener and hardening accelerator enables rapid hardening of this mixture to be obtained.

Finally, the fact of adding a mineral powder whose chemical nature and the granulometry are chosen so as not to reduce the reactivity of the resin, makes it possible to obtain, after having mixed the constituents for a few minutes, a paste having the consistency of mastic, not sticking to the hands and adapted to be easily placed in position during the operation.

DETAILED DESCRIPTION

According to the invention, all the constituents of the cement are chosen so as to be compatible with the biological medium and to have a very low toxicity.

The epoxide resin constituted by a diepoxide of glycidyl ether of bisphenol A advantageously has the following general formula:

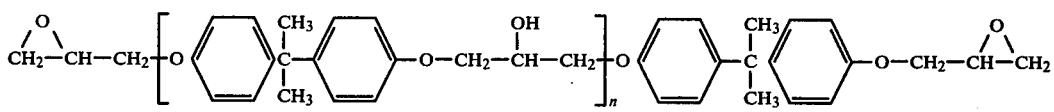

where n is close to 0.2.

By way of example of a resin of this type which may be used, mention may be made of the epoxide resin sold by the firm SHELL under the trademark "EPIKOTE 828", which corresponds to the above formula and has an average molecular weight of about 380, an epoxy equivalent of the order of 190 and a hydroxy equivalent of the order of 1900.

This resin has a good reactivity, a low viscosity (150 poises) and a low toxicity.

Other resins of the same family may be used without the following list being limiting:

Araldite 6010 of the firm CIBA
"Epi-Rez" 510—Jones Dabney Company (Celanese Corp.)
Epotuf 37-140—Reichhold Chemical
ERL 2774—Union Carbide According to the invention, the suppling resin is preferably a polybutadiene comprising hydroxyl groups mainly at the ends of chains and having the following formula:

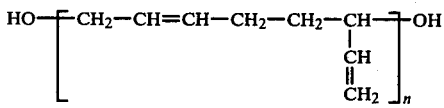

where n has an average value close to 30; for example, the product sold under the trademark "Butarez HTS" by the firm Philips Petroleum which has a good reactivity, an average chain length by weight of about 277 Å, an average rate of hydroxyl by weight of 0.66, a viscosity close to 100 poises at 22° C., and the following distribution of unsaturation:

Cis: 34.6%
Trans: 38.3%
Vinyl: 27.1%

Other resins of the same type with an equal or lower vinyl rate may also be used.

According to the invention, the hardeners used are advantageously compounds with active hydrogen, for example polyamines, polyphenols polyacids, or polyalcohols. Polyamines such as triethylene tetramine of the following formula:

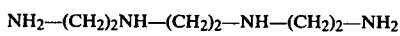

are preferably used.

The hardening accelerator is chosen so as to reduce the time necessary for obtaining hardening of the mixture and to allow hardening thereof in the presence of water.

2-Mercaptoethanol of the formula:

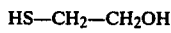

is advantageously used as hardening accelerator.

According to the invention, the mineral filler in powder form has a granulometry chosen as a function of the nature of the resin, particularly its viscosity, to enable a cement to be obtained having the consistency of mastic at the moment of use.

It is advantageously calcium phosphate.

However, other fillers may be used, for example silica, alumina or short fibers of carbon, silica, etc . . .

Furthermore, an agent rendering opaque with respect to X-rays, such as barium sulfate, having a granulometry of the same order as that of the mineral filler is preferably added to this mineral filler.

Finally, an antibiotic may also be added to the mixture.

By way of example, such a mixture may be constituted by:

100 parts by weight of epoxide resin "EPIKOTE 828",
3.9 parts by weight of polybutadiene (BUTAREZ HTS),
13.8 parts by weight of triethylene tetramine,
6.06 parts by weight of 2-mercaptoethanol,
65 parts by weight of calcium phosphate having an average granulometry of about 100μ and
10 to 22 parts by weight of barium sulfate.

According to the invention, the different constituents of the cement composition are preferably packed in separate receptacles which each contain the dose necessary for the final mixture so as to facilitate the surgeon's task when the cement is prepared.

The device for packing the cement of the invention comprises a sealed container made of plastics material, inside which are disposed four receptacles respectively containing the necessary doses of mixture of epoxide resin and suppling resin, of hardener, of accelerator and of mineral filler, the whole, constituted by the container containing the four receptacles, having been subjected to a sterilization.

Sterilization is preferably effected by irradiation by means of ionizing rays.

These receptacles are advantageously constituted by three syringes respectively containing the mixture of resins, the hardener and the accelerator, and a bottle containing the mineral powder; these three syringes and the bottle are placed in a sealed container constituted by a hermetically closed polyethylene bag, which is then sterilized by means of ionizing rays, for example gamma rays, at a dose of about 2.5 Mrad.

Other characteristics and advantages of the invention will be more readily apparent from reading the following example given by way of non-limiting illustration.

In this example, a cement is prepared from the following constituents:

(a) mixture of "EPIKOTE 828" resin and of "BUTAREZ HTS" resin,
(b) hardener consisting of triethylene tetramine, (c) hardening accelerator consisting of 2-mercaptoethanol, and
(d) mineral filler consisting of a mixture of calcium phosphate and barium sulfate.

These different constituents are packed so that they can then be subjected to sterilization by means of ionizing rays.

To this end, a mixture of 23.1 g of "EPIKOTE 828" resin and 0.9 g of "BUTAREZ HTS" is introduced into a hermetic syringe having a volume of about 30 ml and made of polypropylene.

3.2 g of triethylene tetramine and 1.4 g of 2-mercaptoethanol are resepctively introduced into second and third hermetic syringes having a volume of about 5 ml and also made of polypropylene. A polyethylene bottle of about 50 ml is filled with a pulverulent filler constituted by 15 g of calcium phosphate having an average granulometry of 100μ and 2.5 or 5 g of barium sulfate of similar granulometry and is then closed by a screw stopper.

The three syringes and the bottle are placed in a polyethylene bag with a pellet of trioxymethylene, then the bag is closed by heat-sealing and the whole is subjected to sterilization with the aid of ionizing rays at a dose of 2.5 Mrad.

A bag is thus obtained, which contains all the constituents of the cement composition which will be mixed only at the moment of use.

In a surgical operation, the quantity of cement used is small and, in view of the length of the polymerization time, it is necessary to make the mixture of the different constituents under environmental conditions which are as constant as possible so that the dissipation of heat during the reaction is always the same and does not affect the duration of this reaction.

To obtain this result, polyethylene goblets and wooden stirrers of the conventional "tongue-depressor" type are used, which are advantageously disposed in the polyethylene bag and subjected to sterilization.

In fact, it has been observed that the use of beakers

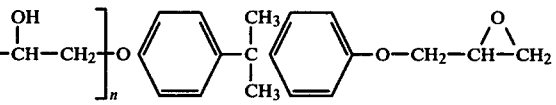

and stirrers made of other materials, for example made of metal or glazed earthenware, leads to longer and less constant polymerization times.

To make the mixture, the mixture of resins, then the filler and finally the hardener and the accelerator are added successively; the mixture is subjected to mixing until the product has the consistency of mastic.

Under normal conditions, the mixture hardens in about 10 mins. and the temperature does not exceed 55° C.

After hardening, it is noted that the voluminal shrinkage is virtually zero whilst, in the case of cement based on methyl methacrylate, this shrinkage is of the order of 3%. Furthermore, this cement has satisfactory mechanical properties. In fact, when it is subjected, after two months in water at 37° C. to tests of traction at a speed of 1 mm per minute, the tensile stress is about 230 bars, which is of the same order as that of the methacrylate cements tested under the same conditions.

Finally, the preservation of the different packed constituents at 5° C. with a view to use thereof, i.e. after introduction into the bag and sterilization of the whole, was tested after 8 months and no change in the mixture was observed.

Furthermore, the results of cutaneous tests made by the Magrusson method have shown that the constituents of the cement were not toxic and did not cause allergies.

What is claimed is:

1. A cement for the fixation of osseous prostheses, obtained by hardening of a mixture comprising:
    (a) at least one epoxide resin having a high reactivity and very low toxicity, consisting of a diepoxide of a glycidyl ether of bisphenol A;
    (b) a reactive, non-toxic suppling resin consisting of a polybutadine having hydroxyl groups mainly at the ends of chains;
    (c) a mineral filler in powder form;
    (d) a hardener capable of reacting with said epoxide resin in order to provoke hardening thereof, and
    (e) a hardening accelerator;
the mixture comprising for 100 parts by weight of the mixture of epoxide resin and suppling resin, 50 to 85 parts by weight of mineral filler, 10 to 20 parts by weight of hardener and 5 to 10 parts by weight of hardening accelerator.

2. The cement of claim 1, wherein the mixture of epoxide resin and of suppling resin comprises at the most 8% by weight of suppling resin.

3. The cement of claim 1, wherein the polybutadiene has the following formula:

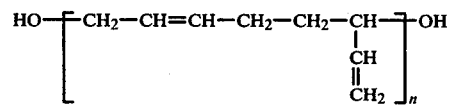

where n has an average value close to 30.

4. The cement of claim 1, wherein the epoxide resin has the following formula:

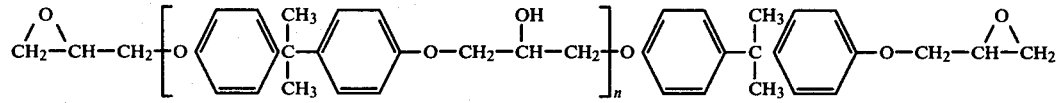

where n is close to 0.2.

5. The cement of claim 4, wherein the epoxide resin has an average molecular weight of about 380, an epoxy equivalent of the order of 190 and a hydroxy equivalent of the order of 1900.

6. The cement of claim 1, wherein the hardener is a polyamine.

7. The cement of claim 6, wherein the hardener is triethylene tetramine.

8. The cement of claim 1, wherein the hardening accelerator is 2-mercaptoethanol.

9. The cement of claim 1, wherein the mineral filler is calcium phosphate.

10. The cement of claim 1, wherein the mineral filler comprises an opaqueing agent consisting of barium sulfate.

11. The cement of claim 1, wherein said mixture further comprises an antibiotic.

12. The cement of claim 1, wherein it comprises, for 100 parts by weight of epoxide resin of formula:

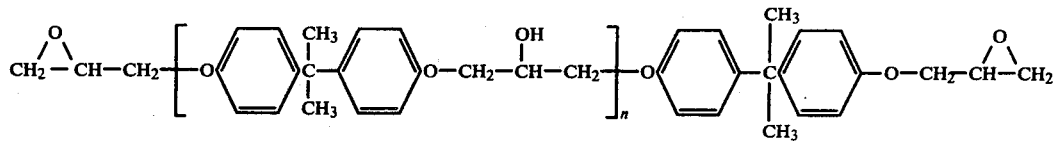

where n is close to 0.2,
3.9 parts by weight of polybutadiene of formula:

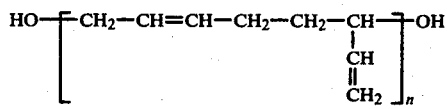

where n has an average value close to 30,
13.8 parts by weight of triethylene tetramine,
6.06 parts by weight of 2-mercaptoethanol,
65 parts by weight of calcium phosphate having an average granulometry of 100μ, and
10 to 22 parts by weight of barium sulfate.

13. A method for fixation of a prostheses to an osseous element, which comprises positioning between the osseous element and the prostheses a mixture comprising:
   (a) at least one epoxide resin having a high reactivity and very low toxicity, consisting of a diepoxide of a glycidyl ether of bisphenol A;
   (b) a reactive, non-toxic suppling resin consisting of a polybutadiene comprising hydroxyl groups mainly at the ends of chains;
   (c) a mineral filler in powder form;
   (d) a hardener capable of reacting with said epoxide resin in order to effect hardening thereof, and
   (e) a hardening accelerator;
the mixture comprising for 100 parts by weight of the mixture of epoxide resin and suppling resin, 50 to 85 parts by weight of mineral filler, 10 to 20 parts by weight of hardener and 5 to 10 parts by weight of hardening accelerator.

* * * * *